Oct. 1, 1940. F. MEILLAND Plant Pat. 426
ROSE PLANT
Filed May 20, 1940
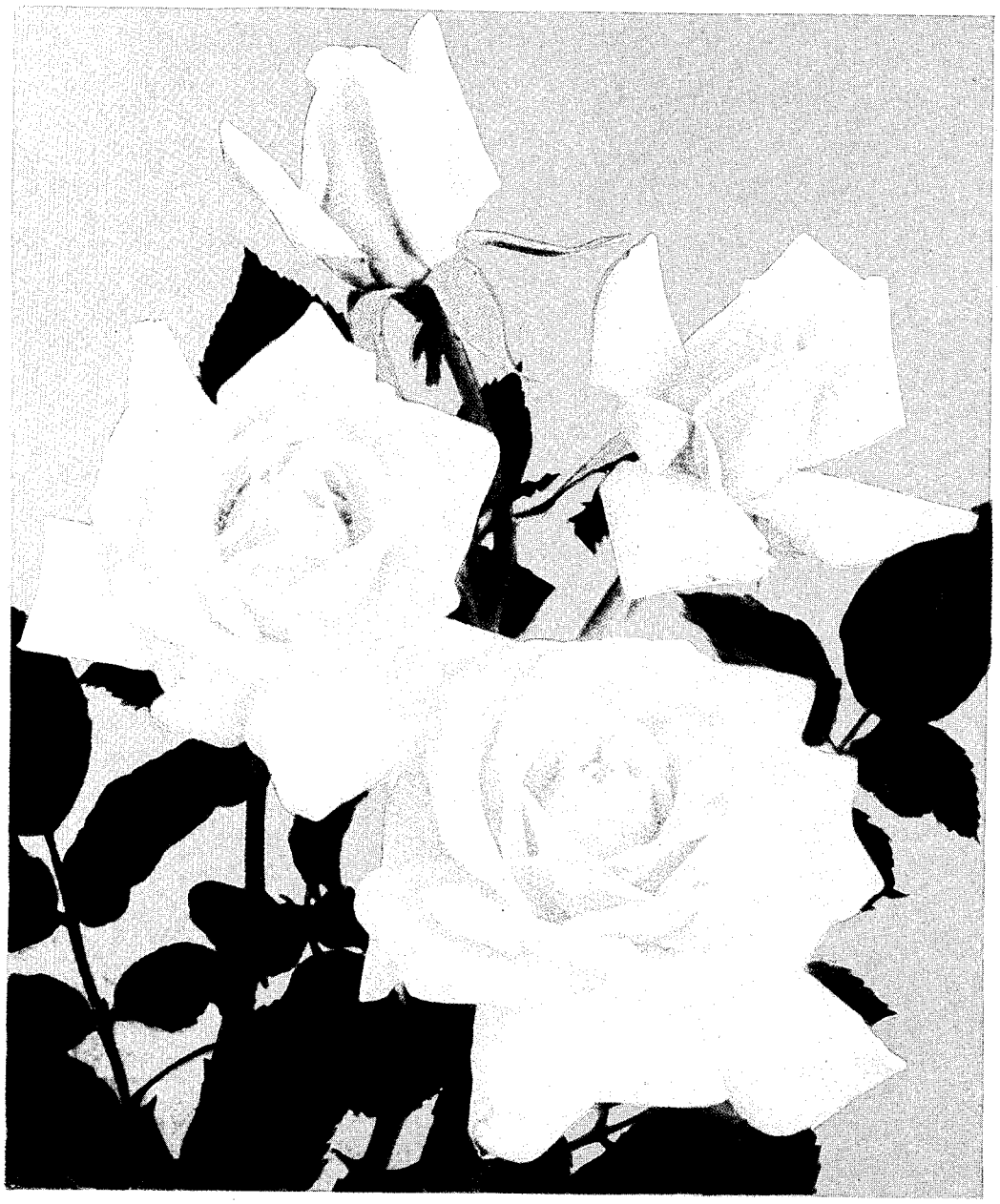
Inventor
Francis Meilland
By Robb & Robb
Attorneys Patented Oct. 1, 1940

Plant Pat. 426

UNITED STATES PATENT OFFICE

426

ROSE PLANT

Francis Meilland, Tassin-les-Lyon, France, assignor to The Conard-Pyle Company, West Grove, Pa.

Application May 20, 1940, Serial No. 336,267

1 Claim. (Cl. 47—61)

The present invention relates to a new and distinct variety of Rose plant, the result of a definite effort to produce an improved hybrid tea of distinctive characteristics and color.

By my particular hybridizing as hereinafter pointed out, I have produced a rose which embodies a combination of vigor of growth with large size and robustness of flower, and a perfectness of very abundant petalage, which is quite unusual, if not entirely unmatched.

These qualities, combined with the delicate pink coloring of the flower, constitute a very desirable variety for both cut flower and garden decoration purposes.

Asexual reproduction by budding shows the novel characteristics to be established.

The following is a detailed description of this new rose, the color terminology employed therein being in accord with Ridgway's Color Standard.

Type: Tall bush; greenhouse-outdoor; seedling; for cut flowers and garden decoration.

Class: Hybrid tea.

Breeding or discovery: Seedling.

*Seed parent.*—Radiance × Souv. de Claudius Pernet.

*Pollen parent.*—Joanna Hill × Countess Vandal.

*Propagation.*—Budding.

*Flower*

Locality where grown: West Grove, Pennsylvania.

Flowers borne: Singly on normal medium length stems.

Quantity of bloom: Free outdoors.

Continuity: Continuous.

Fragrance: Slight; tea.

Bud:

*Peduncle.*—Medium length; medium heavy; medium stiff; Parrot Green, Plate VI; almost smooth; few hairs, Maroon, Plate I.

*Before calyx breaks.* — *Size* — medium. *Form.*—Pointed with foliaceous appendages on the surface of the bud; with stout bristle-like foliaceous parts extending beyond the tip of the bud equal to ¼ or more of its length.

*As calyx breaks.*—*Color*—Shrimp pink shaded Strawberry Pink, Plate I.

*As first petal opens.* — *Size* — medium. *Form* — pointed. *Color:* outside — Shrimp Pink shaded Strawberry Pink, Plate I; inside—Shrimp Pink, Plate I. *Opening*—bud opens up well.

Bloom:

*Size, when fully open.*—Large, 5 inches to 6 inches.

*Petalage.*—Very double from 40 to 60 petals arranged regularly.

*Form.*—High center at first becoming cupped; petals remaining at first very tightly rolled outward and becoming later, at maturity, tightly rolled outward.

Petals: Thick, leathery; with inside and outside satiny.

*Shape.*—*Outside*—obovate; scalloped with one to three notches. Intermediate—obovate, with apex flat. Inside—lanceolate.

This description of a newly opened flower was made from a rose grown outdoors in October, 1939, at West Grove, Pennesylvania:

*Color.*—Outside petal: outside surface—Flesh Pink, Plate XIII; inside surface—Lighter Flesh Pink, Plate XIII. Intermediate petal: outside surface—Orange Pink, Plate II; inside surface—Lighter Orange Pink, Plate II. Inner petal: outside surface—Light Salmon Orange, Plate II; inside surface—Light Salmon Orange, Plate II.

This description was made from a rose that was open for three days outdoors, in October, 1939, at West Grove, Pennsylvania:

*Color*—Outside petal: outside surface—Very Light Flesh Pink, Plate XIII; inside surface—Very Light Flesh Pink, Plate XIII. Inside petal: inside and outside surface—Very Light Flesh Pink, Plate XIII.

*General color effect.*—Newly opened flower—Orange Pink, Plate II, center; outer petals, Flesh Pink, Plate XIII. Three days open—Very Light Flesh Pink, Plate XIII.

*Behavior.*—Drop off cleanly; fading to Light Flesh Pink, Plate XIII.

*Flower longevity.*—On bush in garden five days in October; cut roses grown outdoors kept at living-room temperatures 5–6 days in October.

*Reproductive organs*

Stamens: Medium number arranged about pistils mixed with petaloids.

Filaments: Medium length, most with anthers.

*Color.*—Pinard Yellow, Plate IV.

Anthers: Medium size; open at various times.

*Color.*—Empire Yellow, Plate IV.

Pollen: Moderate.

*Color.*—Mustard Yellow, Plate XVI.

Pistils: Medium number.

Styles: Uneven, short, medium heavy; bunched.

Stigma: Coral Pink, Plate XIII.

Ovaries: Some protruding from calyx.

Hips: Oblong with neck pear-shaped; smooth; fleshy.

*Color.*—Biscay Green, Plate XVII.
Sepals: Fall soon; spear-shaped; recurved.
Seeds: Few; small.

*Plant*

Foliage:
*Leaves.*—Compound of 3–7; normal; medium size; heavy; leathery.
*Leaflets.*—*Shape*—oval with apex acute, base round, simply serrate. *Color*—mature: upper surface—Dark Yellow Green, Plate XXXIII; under surface—Light Elm Green, Plate XVII. *Young*: upper surface—Olive Citrine, Plate XVI, veiled with Liver Brown, Plate XIV; under surface—Light Hellebore Green, Plate XVII, shaded Vandyke Red, Plate XIII.
*Rachis.*—Medium. Upper side—Grooved, hairy. Under side—Moderately thorny.
*Stipules.*—Medium length; narrow, with medium points, turning out at an angle of more than 45°.
*Disease.*—Subject to mildew and blackspot.

Growth:
*Habit.*—Bushy; upright; much branched.
*Growth.*—Vigorous.
*Canes.*—Medium heavy.
*Main Stems.*—Cerro Green, Plate V. *Thorns*—several; medium length; hooked downward with short narrow base. *Prickles*—none. *Hairs*—none.
*Branches.*—Cerro Green, Plate V. *Thorns*—several; medium length; hooked downward with short narrow base. *Prickles*—none. *Hairs*—none.
*New Shoots.*—Citrine, Plate IV, heavily shaded Morocco Red, Plate I. *Thorns*—several; medium length; hooked downward with short narrow base. *Prickles*—none. *Hairs*—none.

I claim:
A new and distinct variety of rose plant, characterized as to novelty by its vigorous growth, the large size and robustness of its flower, the color of the flower, and abundance of petalage thereof, substantially as shown and described.

FRANCIS MEILLAND.